United States Patent [19]

Gold

[11] 4,202,335
[45] May 13, 1980

[54] EXTERNAL CATHETER DRAINAGE DEVICE

[76] Inventor: Lawrence W. Gold, 1286 Larch Ave., Moraga, Calif. 94556

[21] Appl. No.: 880,693

[22] Filed: Feb. 23, 1978

[51] Int. Cl.² .............................................. A61F 5/44
[52] U.S. Cl. .................................................... 128/295
[58] Field of Search ............... 128/2 F, 275, 289–300, 128/281–282; 4/110; 119/14.47, 14.52

[56] References Cited

U.S. PATENT DOCUMENTS

| | | | |
|---|---|---|---|
| 1,105,488 | 7/1914 | Clare | 128/295 |
| 2,565,721 | 8/1951 | Conde | 119/14.52 |
| 2,699,781 | 1/1955 | Koch | 128/295 |
| 2,863,457 | 12/1958 | Barach | 128/295 |
| 3,353,538 | 11/1967 | Carrigan | 128/295 |
| 3,511,241 | 5/1970 | Lee | 128/295 |
| 3,742,953 | 7/1973 | Lee | 128/295 |
| 3,788,324 | 1/1974 | Lim | 128/295 |
| 3,818,867 | 6/1974 | Strange-Hansen | 119/14.47 |
| 3,863,638 | 2/1975 | Rogers et al. | 128/295 |
| 3,916,902 | 11/1975 | Lineberger | 128/295 |
| 4,084,589 | 4/1978 | Kulvi | 128/295 |

Primary Examiner—Robert W. Michell
Assistant Examiner—C. F. Rosenbaum
Attorney, Agent, or Firm—Warren, Chickering & Grunewald

[57] ABSTRACT

An externally applied penile catheter providing an inflatable air chamber extending over and around the penile glans and shaft and applying a uniform pressure thereto for holding the catheter in place and being connected to one end of the drainage tube, the structure additionally co-functioning to anchor the end of the drainage tube in substantial abutment with and in registration with the urethral meatus.

9 Claims, 7 Drawing Figures

EXTERNAL CATHETER DRAINAGE DEVICE

BACKGROUND OF THE INVENTION

1. Field of Invention

The invention relates to condum drainage devices.

2. Description of Prior Art

Although there have been a number of devices proposed in prior art literature for superceding the condom catheter for effecting external catheter drainage of urine, none has solved the acute problems inherent in this type of device, as hereinafter more fully set forth, and none, to applicant's knowledge, has been successfully used in medical practice. Accordingly, the condom drainage device is the only one currently in general use.

A separate prior art statement is being prepared herein, pursuant to C.F.R. 197 and 198.

The penis is a delicate organ covered by thin epithelium and is particularly susceptible to injury or damage occurring by available means of attachment of the catheter and by inadequate drainage, which expose this epithelium to direct trauma and irritation secondary to urine remaining in contact therewith. These conditions may result in obstruction of venous outflow from the penis, resulting in venous stasis, which may in turn result in increased susceptibility of the epithelium to damage, and even possibly result in the occurrence of venous thrombosis of the penis. Attachment of the catheter over a localized or limited area may result in increased likelihood of direct pressure-induced trauma to the penile epithelium. The exposure of the penis to urine, especially when the urine is infected, frequently results in epithelial injury. As a direct result of such injury to the epithelium, there frequently occurs the problem of contusion of the penis, maceration of the penile epithelium, and actual epithelial infection. In the common condom catheter, the penis is obscured from view, and developing injury and infection may go undetected. The foregoing sequence of events makes continued external catheter drainage impossible and results in two possible and less favorable medical alternatives: allowance of urinary incontinence, with its attendant problems, and resort to internal catheter bladder drainage, which is fraught with serious medical problems.

SUMMARY OF THE INVENTION

An object of the present invention is to provide an external catheter drainage device of the character described which may be simply and readily applied and which will apply a substantially uniform securing pressure over substantially the entire organ, thus providing unobstructed arterial blood supply to the penis throughout its entire length and, similarly, a free venous outflow from the penis, thus avoiding venous engorgement, discomfort and a condition known as priapism, a serious medical problem of the penis.

Another object of the present invention is to provide an external catheter drainage device of the character above in which an end of the drainage tube is snubbed into substantial abutment and registration with the urethral meatus, thus effecting a direct drain-off of the urine and substantially eliminating any substantial exposure or contact of the penile epithelium with urine.

A further object of the present invention is to provide an external catheter drainage device which, when in place on the penis, will permit direct viewing of the epithelium to provide early detection of any damage or infection.

The invention possesses other objects and features of advantage, some of which of the foregoing will be set forth in the following description of the preferred form of the invention which is illustrated in the drawings accompanying and forming part of this specification. It is to be understood, however, that variations in the showing made by the said drawings and description may be adopted within the scope of the invention as set forth in the claims.

DETAILED DESCRIPTION OF THE INVENTION

Figure 1:
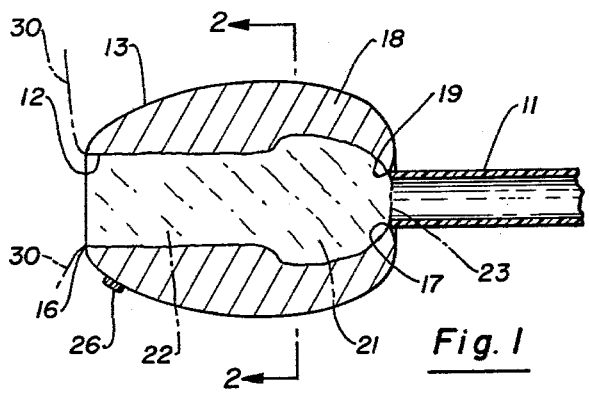
FIG. 1 is a cross-sectional view of an external catheter drainage device constructed in accordance with the present invention.
Figure 2:
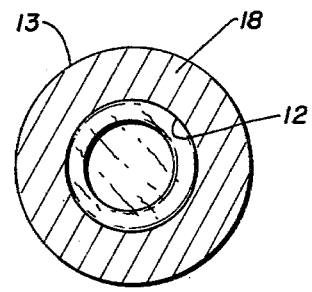
FIG. 2 is a cross-sectional view taken substantially on the plane of line 2—2 of FIG. 1.

The external catheter drainage device of the present invention comprises, briefly, a drainage tube 11; a pair of elongated inner and outer coterminus, impervious members 12 and 13 joined at their opposite ends 16 and 17 to define an air chamber 18 therebetween, the members being joined at ends 17 directly at and to one end 19 of tube 11 with the air chamber 18 contiguous to and extending longitudinally from tube end 19 and with the tube in registration with the interior of inner member 12; inner member 12 being formed of flexible material and being dimensioned together with air chamber 18 to surround and closely conform to the peripheral shape of the penile glans 21 and shaft 22; and chamber 18 being formed for pressurizing to thereby apply a substantially uniform encapsulating pressure on the exterior of the penile glans and shaft and to anchor tube end 19 in substantial abutment and in registration with the urethral meatus 23.

The inflatable nature of the device affords ease of application and removal, and the applying of a uniform pressure over the exterior of the penile glans and shaft maintains a free arterial inflow throughout the length of the penis and a free venous outflow, thus avoiding discomfort and venous engorgement which results in the application of a restricted inflatable cuff, which causes an increase of venous pressure and, potentially, a condition known as priapism, a serious medical problem of the penis. In other words, by applying a more or less uniform pressure around the penis over a large portion of its length and, particularly, uniformly out to the tip, no venous engorgement will take place. The importance here is the avoidance of a limited banding action which would invariably result in an elevation of the venous pressure in the penis distal to the constriction. This problem is avoided by applying uniform pressure from some proximal position on the penile shaft as far out as the arterial blood supply (end of the penis). For purposes of securement and comfort, the device is preferably dimensioned for enclosing and applying a uniform pressure to substantially the entire length of the penis up to the body wall 30.

When the device may be quickly and easily positioned on the penis and inflated and with the device so installed on the penis, the entire organ, with the exception of the urethral meatus, is covered to shield the epithelium from contact with urine. The device thus affords a comfortable, sealed, external drainage system. The large area of contact with the penile shaft and glans assures firm positioning of the device, and the continuation of the area of contact over the penile glans precludes the forming of a reservoir for urine accumulation and contact with the penile epithelium. Snubbing of the end 19 of drainage tube 11 against the urethral meatus and in registration therewith assures the direct and immediate drainage of urine away from the penis.

As a further feature of the present invention, members 12 and 13 are formed of transparent material for visual inspection through the members and air chamber of the penile epithelium. This may be accomplished, as here shown, by forming the members of thin, flexible sheets of transparent plastic. As here shown, these sheets are in tubular form defining an elongated air chamber 18 therebetween. An air inlet valve 26 is here provided on member 13 to provide inflation of the air chamber. A lure lock adapted for receipt of a standard hypodermic-type inflation device may be used. The thin flexible sheet construction of the device affords a convenient rolling up of the device for subsequent convenient unrolling onto the penis up to the body wall 30.

Figure 3:
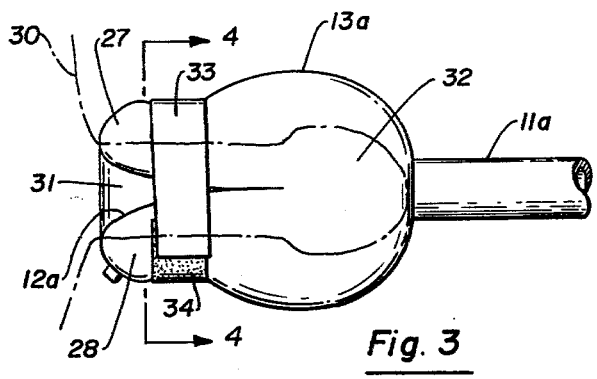
FIG. 3 is a side elevation of a modified form of the device.
Figure 4:
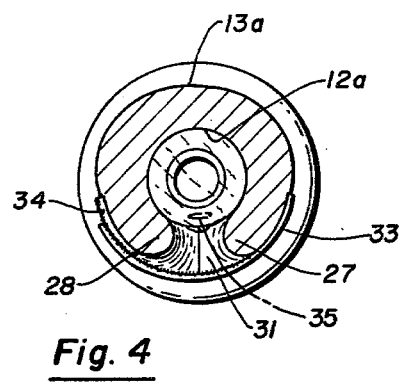
FIG. 4 is a cross-sectional view taken substantially on the plane of line 4—4 of FIG. 3.

A modified form of the invention is illustrated in FIGS. 3 and 4, including means for relieving pressure on the urethral canal and providing an alternate and convenient form of attachment. In this form of the invention, inner and outer chambers 12a and 13a are formed with separable sections 27 and 28 at their end portions 31 for receiving and wrapping around the penile shaft, the sections preferably having an adjacent closed portion 32 into which the penile glans and adjacent shaft may be inserted. Flexible banding means 33 may be placed in encircling position to sections 27 and 28 to hold them in their wrapped-around position, as seen in FIGS. 3 and 4. The banding means may comprise a simple flexible strip secured at one end to one of the sections 27-28 and having means of attachment such as a Velcro pad 34 on the other section. Members 12a and 13a are here again formed of thin, flexible sheets of transparent material, enabling the opening out of sections 27 and 28 for receiving and wrapping around the penis to facilitate attachment and to permit subsequent inspection of the penile epithelium for injury or infection.

The means for relieving the pressure on the urethral canal 35 here comprises the open portion 31 between the confronting ends of sections 27 and 28, which are spaced apart for straddling the urethral canal so that the latter is located within the open portion 31 for minimizing pressure on the canal. Additionally, the banding strap 33 provides adjustment of the banding pressure on the penile shaft.

Figure 5:
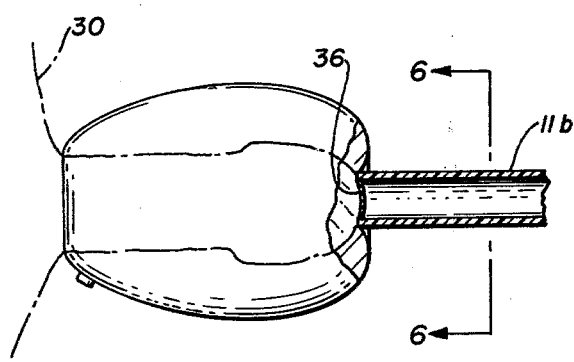
FIG. 5 is a side elevation partially in section of a further modified form of the invention.
Figure 6:
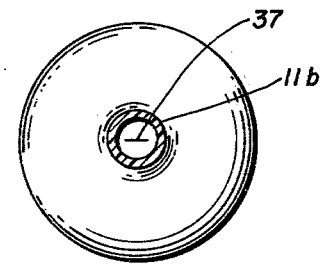
FIG. 6 is a cross-sectional view taken substantially on the plane of line 6—6 of FIG. 5.
Figure 7:
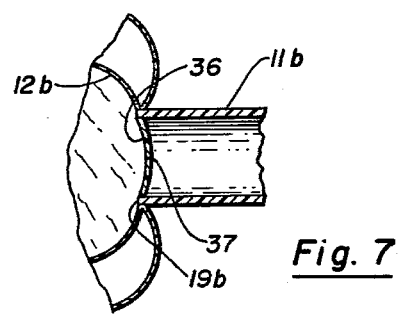
FIG. 7 is an enlarged fragmentary cross-sectional view of a portion of the device shown in FIG. 5.

A further embodiment of the invention is illustrated in FIGS. 5, 6 and 7, wherein a normally closed one-way check valve 36 is mounted interiorly of inner member 12b at end 19b of tube 11b and constructed to open in response to urethral discharge pressure. Valve 36 may comprise a simple membrane mounted across and closing tube end 19b, as seen in FIGS. 5 and 7, and being formed with a normally closed slit 37, the membrane flexing in response to urethral discharge pressure to open slit 37 for one-way urine discharge.

What is claimed is:

1. An external catheter drainage device dimensioned to fit over and surround the penile glans of the user and to extend over the penile shaft of the user, and a drainage tube therefor;
    said device comprising:
        a pair of elongated inner and outer coterminous impervious members extending substantially over the full length of said device and joined at their opposite ends to define a continuous air chamber therebetween over the length of said device, said members being joined at one end directly at and to one end of said tube with said air chamber contiguous to and extending longitudinally from said tube end and with said tube in registration with the interior of said inner member;
        said inner member being formed of a thin flexible sheet having a thinness and flexibility such as to lay in substantially continuous contact with the exterior contours of the penile glans and shaft and being dimensioned together with said air chamber to surround and closely conform to the peripheral shape of the penile glans and shaft; and
        said chamber being formed for pressurizing to thereby apply a substantially uniform encapsulating pressure on the exterior of the penile glans and shaft and to anchor said tube end in substantial abutment and in registration with the urethral meatus.

2. The device of claim 1, said members being dimensioned to extend said air chamber over substantially the full length of the penile shaft.

3. The device of claim 1, said members being formed of transparent material for visual inspection through said members and air chamber of the penile epithelium.

4. The device of claim 1, said members comprising thin flexible sheets in tubular form defining an elongated annular air chamber therebetween.

5. The device of claim 1, said members being formed with separable segmental toroidal air chamber sections at their proximal end dimensioned for receiving and wrapping around the penile shaft on opposite sides of and spaced from the urethral canal for relieving pressure on said canal.

6. The device of claim 5, said members comprising thin flexible sheets of transparent material for visual inspection through said members and air chamber of the penile epithelium.

7. The device of claim 1, and a normally closed one-way check valve mounted interiorly of said inner member at said tube end and opening only in response to urethral discharge pressure.

8. The device of claim 7, said valve comprising a membrane mounted across and normally closing said tube end and being formed with a normally closed slit, said membrane flexing in response to said pressure to open said slit.

9. The method of applying an external catheter drainage device to the penis of the user comprising:
    encapsulating the penile glans and shaft within an inflatable elongated toroidal air chamber having a thin flexible interior wall providing substantially continuous contact with the exterior contours of the penile glans and shaft and a contiguous drainage tube having its proximal end connected to the distal end of said air chamber and wall and in registration with the interior of said interior wall; and inflating said chamber to displace said wall into a substantially uniform encapsulating pressurized fit about the penile glans and shaft to retain the device thereupon and to seal the penis from contact with urine and to snub the proximal end of said drainage tube against the urethral meatus.

* * * * *